United States Patent
Sawabe et al.

(10) Patent No.: US 9,927,376 B2
(45) Date of Patent: Mar. 27, 2018

(54) TEMPLATE DEFECT INSPECTION METHOD

(71) Applicant: TOSHIBA MEMORY CORPORATION, Tokyo (JP)

(72) Inventors: Tomoaki Sawabe, Tokyo (JP); Shinobu Sugimura, Kanagawa (JP); Ryosuke Yamamoto, Kanagawa (JP); Seiji Morita, Tokyo (JP)

(73) Assignee: Toshiba Memory Corporation, Tokyo (JP)

( * ) Notice: Subject to any disclaimer, the term of this patent is extended or adjusted under 35 U.S.C. 154(b) by 0 days.

(21) Appl. No.: 15/265,409

(22) Filed: Sep. 14, 2016

(65) Prior Publication Data

US 2017/0269005 A1    Sep. 21, 2017

(30) Foreign Application Priority Data

Mar. 15, 2016   (JP) .................................. 2016-051353

(51) Int. Cl.
*G01N 21/00* (2006.01)
*G01N 21/956* (2006.01)
*G01N 21/21* (2006.01)

(52) U.S. Cl.
CPC ........... *G01N 21/956* (2013.01); *G01N 21/21* (2013.01)

(58) Field of Classification Search
CPC  G02B 5/3058; G02B 5/3075; G02B 27/2214; G02B 27/26; G02B 5/1828; G02B 5/30; G02B 6/0028; G02B 6/003; G02B 6/0068; G02B 17/0892; G02B 26/001; G02B 26/0841; G02B 3/0006; G02B 5/3016
See application file for complete search history.

(56) References Cited

U.S. PATENT DOCUMENTS

| | | | |
|---|---|---|---|
| 8,334,977 B2* | 12/2012 | Fukazawa | G01N 21/21 356/237.1 |
| 2002/0151092 A1* | 10/2002 | Li | G01R 31/307 438/16 |
| 2005/0088188 A1* | 4/2005 | Borden | G01N 21/95607 356/237.5 |
| 2010/0177312 A1* | 7/2010 | Fujimori | G01N 21/956 356/364 |
| 2010/0308513 A1 | 12/2010 | Kashiwagi et al. | |

(Continued)

FOREIGN PATENT DOCUMENTS

JP    2010-287625    12/2010
JP    2012-18096     1/2012
(Continued)

*Primary Examiner* — Michael P Stafira
(74) *Attorney, Agent, or Firm* — Finnegan, Henderson, Farabow, Garrett & Dunner, L.L.P.

(57) ABSTRACT

A template defect inspection method using an optical system includes emitting linearly polarized light to a template having a metal film formed on at least part of a concave-convex structure that is formed on a substrate and that has a line-and-space pattern, acquiring information on a polarization-rotated component, which is different from linearly polarized light incident on the template, of light reflected by the template in accordance with the emission thereto, converting the acquired information on the polarization-rotated component into an electrical signal, and processing the electrical signal.

14 Claims, 7 Drawing Sheets

(56) References Cited

U.S. PATENT DOCUMENTS

| | | |
|---|---|---|
| 2012/0038911 A1 | 2/2012 | Yoshihiro et al. |
| 2014/0232032 A1 | 8/2014 | Yoshikawa et al. |
| 2014/0235739 A1 | 8/2014 | Morita |
| 2015/0054941 A1 | 2/2015 | Ogawa |
| 2015/0224702 A1 | 8/2015 | Asano et al. |

FOREIGN PATENT DOCUMENTS

| | | |
|---|---|---|
| JP | 2012-42216 | 3/2012 |
| JP | 2012-243799 | 12/2012 |
| JP | 5297930 | 9/2013 |
| JP | 5554164 | 7/2014 |
| JP | 2014-162016 | 9/2014 |
| JP | 2014-165203 | 9/2014 |
| JP | 2014-216365 | 11/2014 |
| JP | 2015-64569 | 4/2015 |
| JP | 2015-153871 | 8/2015 |
| JP | 5771256 | 8/2015 |
| WO | WO 2015/137164 A1 | 9/2015 |

* cited by examiner

| hp (nm) | S/N RATIO | |
|---|---|---|
| | QUARTZ | QUARTZ + METAL FILM |
| 20 | 1 | 1.8 |
| 15 | 1 | 1.7 |
| 12 | 1 | 1.65 |

| hp (nm) | METAL FILM THICKNESS (nm) | | | | |
|---|---|---|---|---|---|
| | 1 | 2 | 3 | 4 | 5 |
| 20 | ○ | ○ | ○ | ○ | × |
| 15 | ○ | ○ | ○ | × | × |
| 12 | ○ | ○ | × | × | × |

TEMPLATE DEFECT INSPECTION METHOD

CROSS REFERENCE TO RELATED APPLICATIONS

This application is based upon and claims the benefit of priority from prior Japanese Patent Application No. 2016-051353 filed on Mar. 15, 2016 in Japan, the entire contents of which are incorporated herein by reference.

FIELD

Embodiments described herein relate generally to a template defect inspection method.

BACKGROUND

Nanoimprinting is known as a technique of forming fine patterns at low cost. The nanoimprinting is a method of pressing a template having concaves and convexities, which correspond to a pattern to be formed on a substrate, onto a curable organic material layer applied on the substrate surface, followed by radiation, heating, etc. to harden the curable organic material, and separating the template from the curable organic material layer, thereby transferring the pattern onto the substrate. If there are defects on the template surface, the defects are also transferred onto the substrate surface. For this reason, defect inspection is performed on the template or the transferred pattern.

In recent years, with increase in degree of integration of semiconductor devices, microfabrication has progressed for the size of each device and the width of wirings, gates, etc. that constitute each device. For example, a half pitch (expressed as an hp, hereinafter), which is half of a line-and-space pattern, has become smaller than 100 nm. For this reason, defect inspection is required to detect extremely small pattern defects. A known defect inspection method is to detect micro defects by using a short wavelength laser as a light source. There are other known inspection equipment and method which are capable of highly accurate inspection with a minimum decrease in intensity of inspection light, by using linearly polarized light as the inspection light and adopting an optical system having a polarization beam splitter. However, the known inspection equipment and method have a difficulty in accurate detection of micro defects due to optical resolution limits and the like.

DETAILED DESCRIPTION

A template defect inspection method according to the present embodiment is a template defect inspection method using an optical system, which includes emitting linearly polarized light to a template having a metal film formed on at least part of a concave-convex structure that is formed on a substrate and that has a line-and-space pattern, acquiring information on a polarization-rotated component, which is different from linearly polarized light incident on the template, of light reflected by the template in accordance with the emission thereto, converting the acquired information on the polarization-rotated component into an electrical signal, and processing the electrical signal.

Hereinafter, embodiments of the present invention will be explained with respect the drawings.

First Embodiment

A template defect inspection method according to a first embodiment will be explained.

Figure 1:
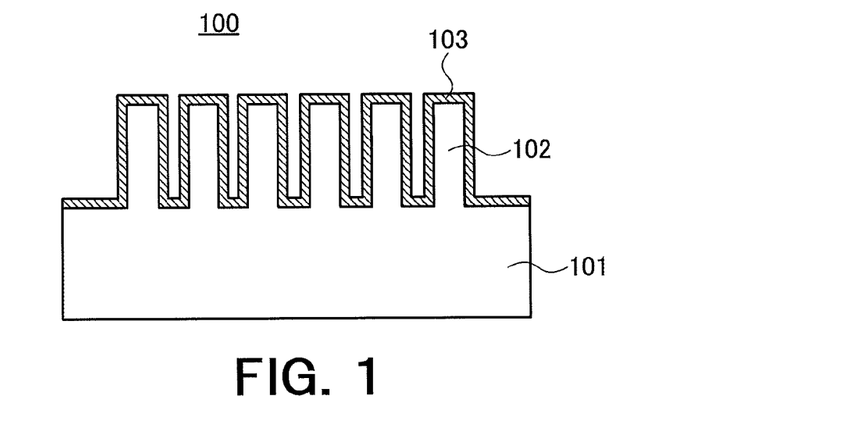
FIG. 1 is a sectional view showing an example of a template to be inspected.

An example of a template to be inspected is shown first in FIG. 1. A template 100 has a substrate 101, a concave-convex structure 102, and a metal film 103. Although not shown, the template 100 may have other components such as an alignment mark on the substrate 101 in addition to the concave-convex structure 102. The template 100 is, for example, a template for nanoimprinting. The substrate 101 is, for example, a quartz substrate. The concave-convex structure 102 is made of, for example, quartz, which is formed by patterning, for example, by electron beam lithography. As described later, it is preferable that a line-and-space pattern of the concave-convex structure 102 has an hp smaller than a resolution limit that is determined by a wavelength of a light source of an inspection optical system and a numerical aperture of an objective lens of the inspection optical system, which will be described later. It is preferable that the concave-convex structure 102 has a height that is about ¼ of the wavelength of the light source. However, the height may be designed as required depending on the hp of the concave-convex structure 102.

As described later, the metal film 103 preferably has a small surface roughness which is, more preferably, equal to or less than 3 nm, which preferably does not increase edge roughness of the concave-convex structure 102. It is desirable that the metal film 103 has a strong interaction with incident light from a light source. Practically, it is preferable that the metal film 103 is made of a metal that contains at least one element selected from among W, Ta, Ti and Ni. The metal film 103 may be an alloy of at least one metal, which is selected from among W, Ta, Ti and Ni as a main component, and another metal such as Cr, Mo, Al or Ag. The metal film 103 preferably has a film thickness that is about 5% to 20% of the hp. It is preferable that the metal film 103 is present on the upper surface of and at least part of the side or bottom surface of the concave-convex structure 102, with a film thickness of about 5% to 20% of the hp. The metal film 103 may be formed on the entire surface of the template 100 or only on part of the concave-convex structure 102.

Figure 2A:
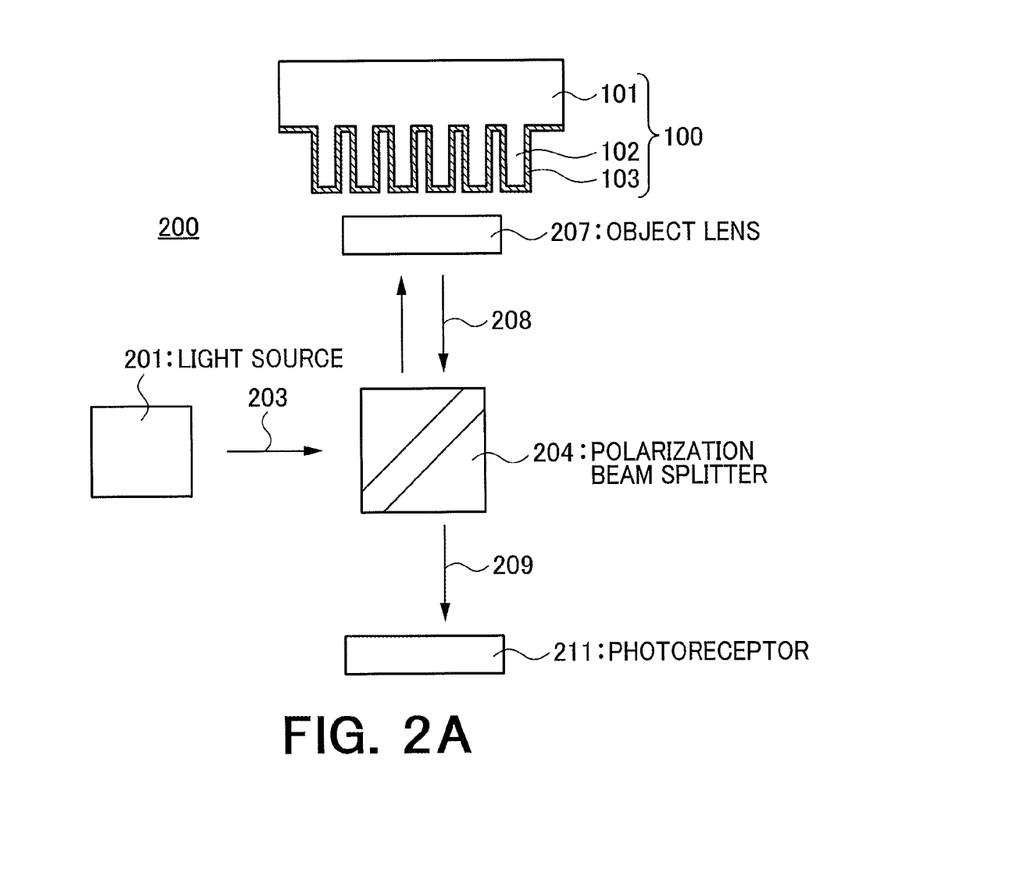
FIG. 2A is a block diagram showing an example of an inspection optical system used in a first embodiment.

FIG. 2A shows an example of an inspection optical system 200. The inspection optical system 200 has, for example, a light source 201, a polarization beam splitter 204, an objective lens 207, and a photoreceptor 211. By adopting an inspection optical system such as shown in FIG. 2A, in incident light 203 emitted from the light source 201, a specific linearly polarized component only is reflected by the polarization beam splitter 204, passes through the objective lens 207, and is then emitted to the template 100. Reflected light 208 reflected on the template 100 is subjected to polarization rotation caused by structural birefringence on the concave-convex structure 102 formed on the template 100. In the reflected light 208 subjected to the polarization rotation, a linearly polarized component, the same as the incident light 203, is reflected toward the light source 201 by the polarization beam splitter 204. In the reflected light 208 subjected to the polarization rotation, a polarization-rotated component 209, which has been subjected to the polarization rotation by the template 100 to be in a polarized state different from the incident light 203, passes through the polarization beam splitter 204 and is incident on the photoreceptor 211. As for the photoreceptor 211, for example, an imaging device is used. Light captured by the imaging device is processed by a signal processing unit and formed into an image by an image forming unit.

As described later, in the present embodiment, the inspection optical system preferably has a polarization-rotation change amount provider that detects an amount of change in polarization rotation, from linearly polarized light incident on the template 100, of linearly polarized light reflected by the template 100, and provides the amount of change in polarization rotation to an imaging device. As the polarization-rotation change amount provider, in the present embodiment, the polarization beam splitter 204 is used. What is shown here is just an example. In order to achieve the effect of the present embodiment, any types of optical systems can be used, as long as the optical systems can supply a component, which is changed from linearly polarized light incident on the template 100, of reflected light from the template 100 after the linearly polarized light is incident thereon, to an imaging device, using a variety of optical devices such as a polarizer or an analyzer. Such optical systems described above can accurately detect defects, not only by the example shown here.

In the present embodiment, and in the inspection optical system shown in FIG. 2A, 90°-linearly polarized light is incident on the template 100. However, like an inspection optical system shown in FIG. 2B, by providing a proper wave plate 205 and a Faraday rotator 206 between the polarization beam splitter 204 and the objective lens 207, the angle of linearly polarized light to be incident on the template 100 may be controlled in accordance with the arrangement of the concave-convex structure 102 provided on the template 100.

Figure 2B:
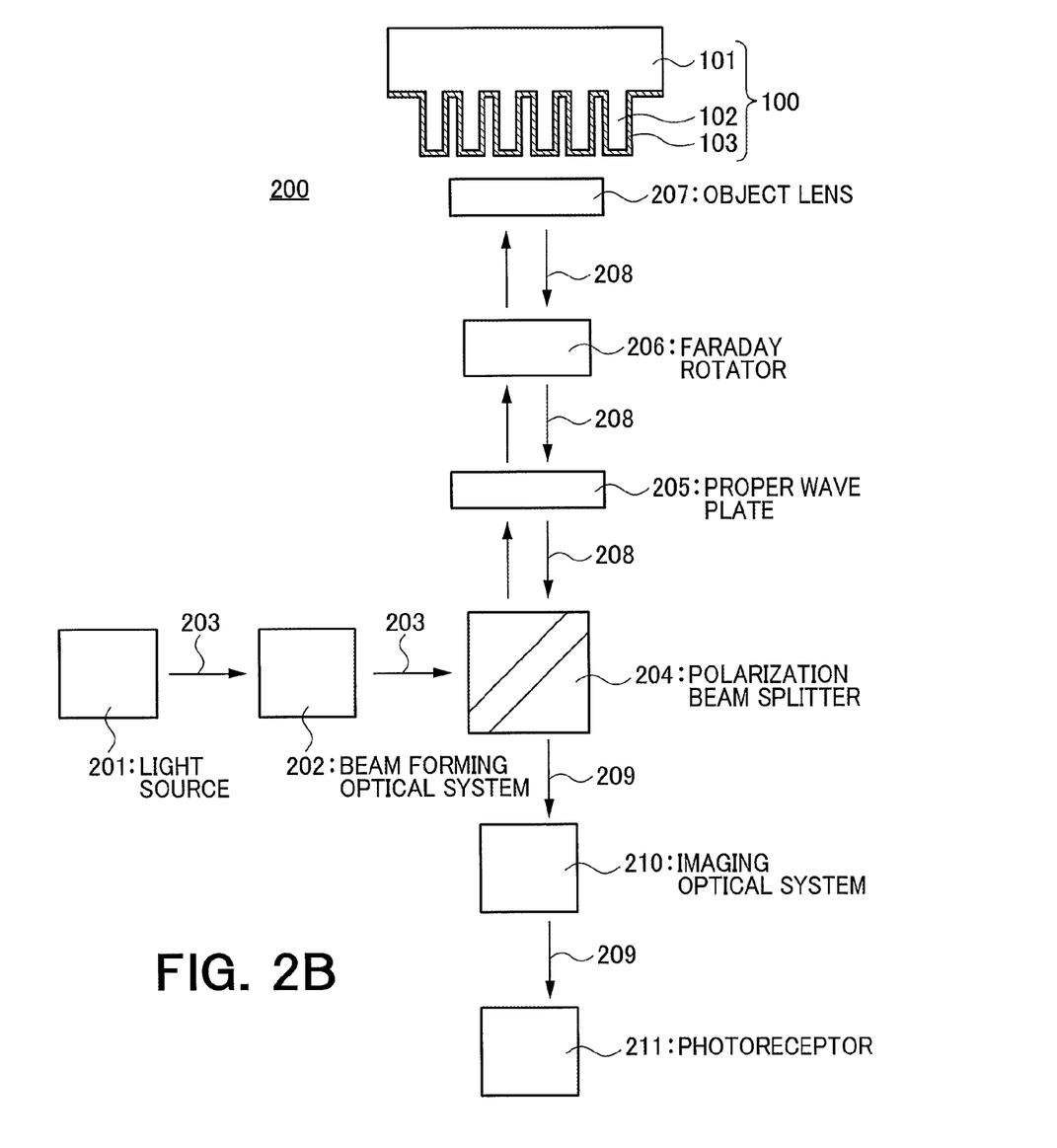
FIG. 2B is a block diagram showing another example of the inspection optical system used in the first embodiment.

The Faraday rotator 206 has an optical material that allows light to pass therethrough and a coil wound around the optical material. For the optical material, a material that has a high transmittance to light from a light source is used. The coil is wound so that, by making a current flow therethrough, a magnetic field parallel to the light travel direction is applied to the optical material.

The Faraday rotator 206 rotates the polarization plane of light by the Faraday effect. The Faraday effect is a phenomenon in which two components (clockwise circular polarized light and anticlockwise circular polarized light) of linearly polarized light show a difference in phase velocity when the linearly polarized light is incident on an optical material and a magnetic field is applied in the same direction as the light travel direction, which results in rotation of the polarization plane of light (linearly polarized light) emitted from the optical material due to a phase difference at the exit.

In the optical system shown in FIG. 2B, the Faraday rotation angle of the Faraday rotator 206 is set so that light scattered at the edge roughness of a line-and-space is not incident on the imaging device 211. With this setting, defects can be accurately detected.

The polarization direction of light that illuminates the template 100 is changed by both of the Faraday rotator 206 and the half wave plate 205. The Faraday rotator 206 can change the angle of a polarization direction of light by varying the magnitude a magnetic field applied to the optical material. The half wave plate 205 gives an optical path difference corresponding to a half wavelength of light when linearly polarized light components that vibrate in mutually perpendicular directions pass through the half wave plate 205, capable of rotating the polarization angle without varying the intensity of passing light. The half wave plate 205 can freely vary the rotation angle by providing a rotary mechanism.

In the above description, what is descried as an example of the Faraday rotator is that a magnetic field is applied to an optical material by making a current flow through a coil. However, not only using an electromagnet as the above example, the Faraday rotator may use a permanent magnet or a combination of the electromagnet and permanent magnet. Light refraction index varies almost linearly with temperature. Therefore, the electromagnet may cause a temperature distribution to the coil, resulting in aberration. Such a problem can be avoided by using the permanent magnet. In this case, it is preferable that the type or the number of permanent magnets can be changed so that a magnetic field is generated in accordance with a required rotation angle. When the permanent magnet and electromagnet are combined, it is possible that, in addition to provide the permanent magnet to generate a basic magnetic field, the electromagnet generates a magnetic field only for giving a required rotation angle. With such a configuration, replacement of the permanent magnet, or the like, is not necessary and temperature increase can be restricted to a minimum degree.

The inspection optical system shown in FIG. 2B is provided with a beam forming optical system 202 for forming the shape of incident light between the light source 201 and the polarization beam splitter 204, and an imaging optical system 210 for imaging light to the imaging device 211 between the polarization beam splitter 204 and the imaging device 211. The beam forming optical system 202 and imaging optical system 210 may be used in the inspection optical system shown in FIG. 2A. In inspection of the line-and-space pattern, by providing a half wave plate as the wave plate, 45°-polarized light is incident on the template 100 to make it possible to inspect a line-and-space in the lateral direction and a line-and-space in the vertical direction at the same time. For example, a Faraday rotator may be used to inspect one and the same template two times with 90°-linearly polarized light and 180°-linearly polarized light to inspect a line-and-space pattern in the lateral direction and a line-and-space pattern in the vertical direction.

Figure 3:
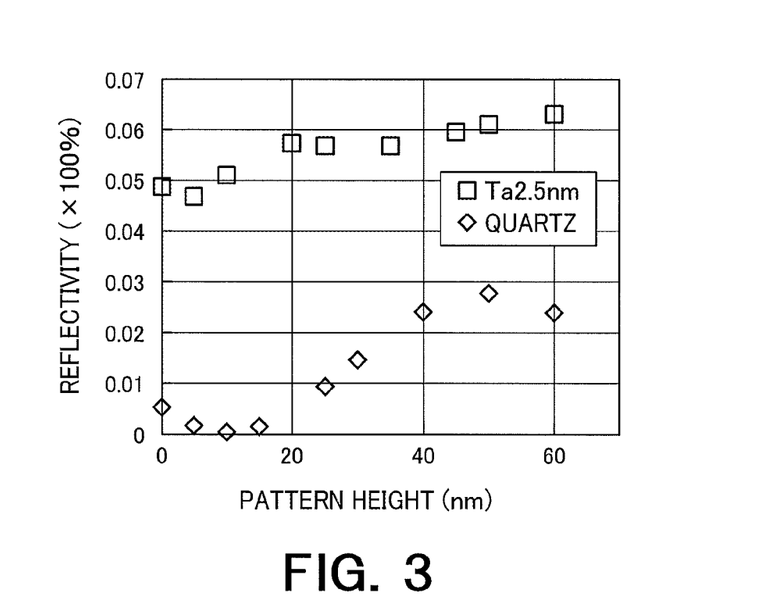
FIG. 3 is a view showing pattern height dependency of reflectivity of a template.
Figure 4:
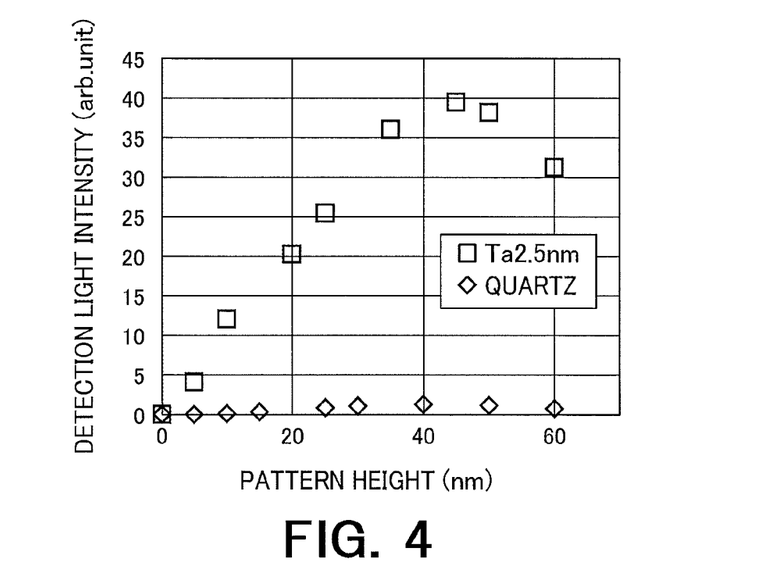
FIG. 4 is a view showing pattern height dependency of intensity of light detected by an optical system.

FIG. 3 shows a result of height dependency of intensity (reflectivity) of reflected light from a template simulated by a finite-difference time-domain method. FIG. 4 shows a result of dependency of intensity (intensity of detected light) of a polarization-rotated component, which is detected by the optical system 200 shown in FIG. 2A, on the height of the concave-convex structure 100. In FIGS. 3 and 4, simulations were performed in a state where the quartz template 100 was not formed with the metal film 103 and in a state where the quartz template 100 was formed with the metal film 103 at a thickness of 2.5 nm. Ta was used for the metal film 103. The wavelength of the light source 201 was 200 nm. As understood from FIGS. 3 and 4, by forming the metal film 103, the reflectivity of the template 100 is improved and polarization rotation is increased due to change in structural birefringence, resulting in increase in intensity of both of the reflected light and light detected by the optical system 200. As described later, since the intensity of detected light is low at defect portions, when the intensity of detected light on a line-and-space is increased, a contrast ratio between the defect portions and the line-and-space becomes higher, which enables accurate detection of micro defects.

Both of the intensity of reflected light and the intensity of detected light showed a peak intensity around 50 nm, about ¼ of 200 nm that is a wavelength of the light source 201. It is considered that the intensity increased due to the interference of reflected light. It is preferable that the height of the concave-convex structure 102 is about ¼ of the wavelength of the light source 201. Nevertheless, since the height of the concave-convex structure 102 is designed in accordance with the hp of the concave-convex structure 102, the height is not always necessarily be ¼ of the wavelength of the light source 201.

Figure 5:
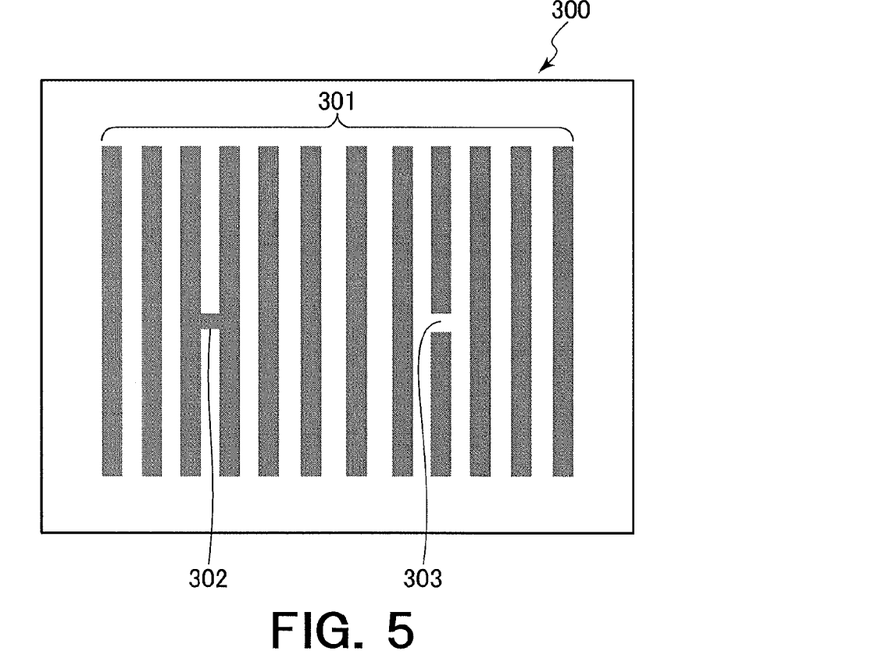
FIG. 5 is a plan view showing an example of an inspection area of a template.

FIG. 5 shows a schematic view of an inspection area 300 of a template. The inspection area 300 has a pattern forming area 301. The pattern forming area 301 has a short defect 302 and an open defect 303. In this example, a line-and-space is formed in the vertical direction in FIG. 5, in which the short defect 302 is a defect in which lines are connected to each other and the open defect 303 is a defect in which lines are disconnected from each other.

Figure 6:
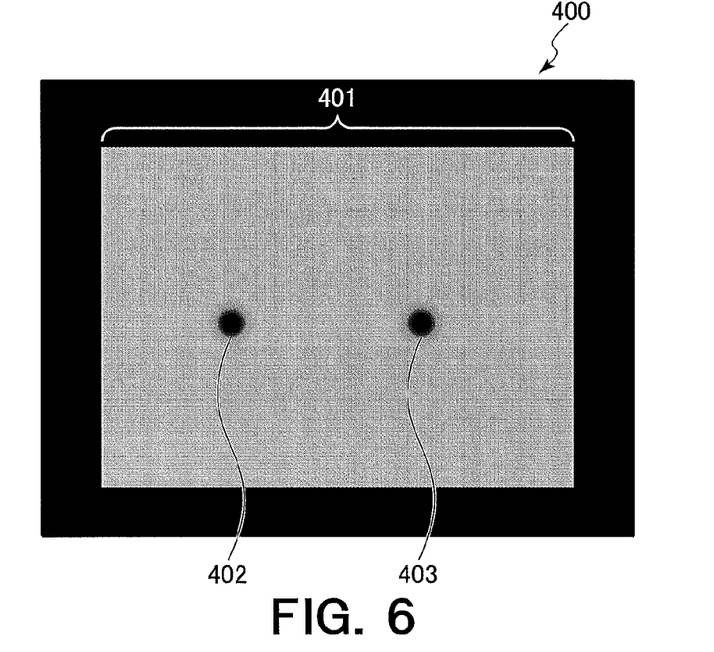
FIG. 6 is a photograph showing an inspected image of the inspection area shown in FIG. 5 inspected for defects by an inspection optical system.

FIG. 6 shows an inspected image 400 of the inspection area 300 shown in FIG. 5, which was inspected for defects by the optical system 200 shown in FIG. 2A. In FIG. 6, an area corresponding to the pattern forming area 301 is an inspection area 401. The optical system 200 detects a component subjected to polarization rotation caused by structural birefringence on the concave-convex structure 102 formed in the pattern forming area 301, so that the inspection area 401 is displayed in the inspected image 400 at a high contrast. In the inspection area 300, an area with no patterns formed is displayed at a low contrast. Portions 402 and 403, where the short defect 302 and the open defect 303 are present, respectively, are displayed at a low contrast and detected as defects, because polarization rotation rarely occur in these portions.

The defect detection accuracy can be evaluated by means of a signal-to-noise ratio (S/N ratio). The S/N ratio can be calculated by dividing a signal by a noise where the signal is an absolute value of a difference between a signal intensity in the defect portions 402 and 403, and an average value of a signal intensity in the inspection area 401, and the noise is the standard deviation of the signal intensity in the inspection area 401. It is considered that a higher S/N ratio gives a higher defect detection accuracy.

Templates to be inspected were actually prepared by electron beam lithography to have a concave-convex structure formed having a short defect and an open defect on a quartz substrate. Defect inspection was performed before and after the formation of a metal film on the templates, to calculate an S/N ratio. The templates with defects had 20 nm, 15 nm and 12 nm, respectively, in hp, having patterns extremely smaller than the resolution limit of an optical system, each with a defect size being almost the same as the hp and being smaller than the resolution limit of the optical system. As for the metal film, 2 nm-thick NiTa was formed by sputtering.

Figure 7:
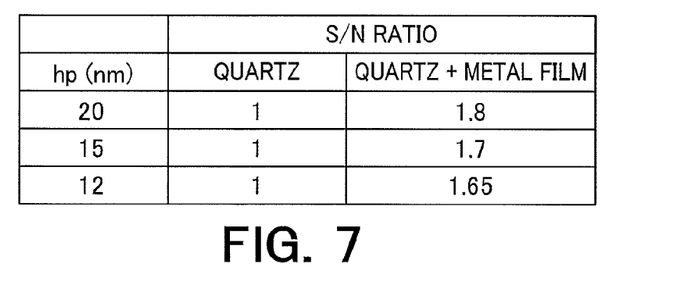
FIG. 7 is a view showing a relative S/N ratio of a quartz template having a metal film formed thereon to an S/N ratio in defect detection of a quartz template with no metal film formed thereon.

FIG. 7 shows a relative S/N ratio of each of quartz templates having the metal film formed thereon to an S/N ratio of 1 in defect detection of a quartz template with no metal film formed thereon, for templates to be inspected having 20 nm, 15 nm and 12 nm, respectively, in hp. It is found that, by forming the metal film, the S/N ratio in defect detection was improved to detect defects at high accuracy. The S/N ratio in defect detection was improved at every hp by forming the metal film.

As a comparative example, inspection was performed by emitting circular polarized light, instead of linearly polarized light, to templates and simply detecting reflected light from the templates. The result is that no defects were found in the case of a quartz substrate and also of a substrate having a metal film formed on quartz.

According to the above description, it is found that a defect inspection method with a metal film formed on a template, as in the case of the present embodiment, is effective especially with the use of an optical system that detects an amount of change in polarization rotation, from linearly polarized light incident on a template, of linearly polarized light reflected by the template after being incident thereon.

Figure 8:
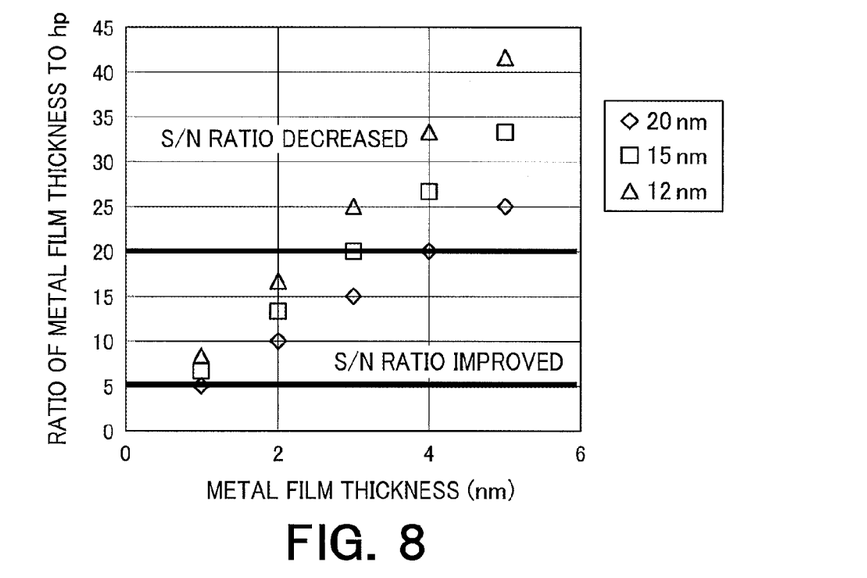
FIG. 8 is a view showing metal film thickness dependency of a ratio of metal film thickness to an hp.
Figure 9:
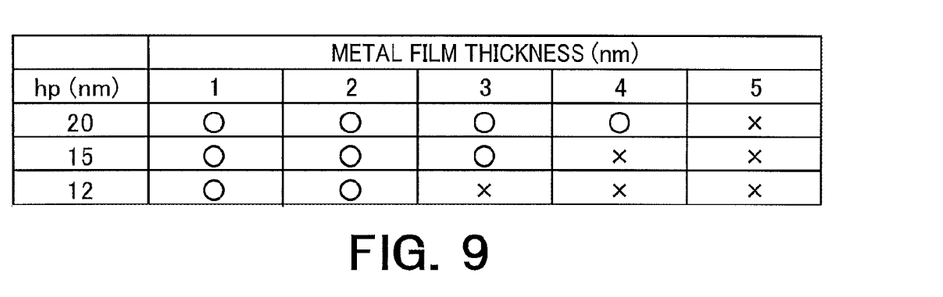
FIG. 9 is a view showing improvement effects of an S/N ratio when the metal film thickness to the hp is varied.

FIGS. 8 and 9 show results of the same inspection as that described above, with change in metal film thickness. In FIG. 9, symbols ○ (circle) and x indicate improvement and no improvement in S/N ratio, respectively. As understood from FIGS. 8 and 9, the S/N ratio was improved in the case where the metal film has a thickness that is 5% to 20% of the hp. This is because, in the case of a thick metal film, the line-and-space becomes so small that there is no occurrence of polarization rotation caused by structural birefringence on the concave-convex structure. In order to perform inspection at high accuracy, it is preferably that the metal film has a thickness that is about 5% to 20% of the hp. In the case of a tall concave-convex structure, it is difficult to form a metal film on the bottom of the concave-convex structure, compared to the top thereof. However, as long as the metal film is formed on the top of, and at least part of the side and bottom surfaces of the high concave-convex structure, the metal film has a strong interaction with a polarized component of inspection light, which enables accurate defect detection.

Figure 10:
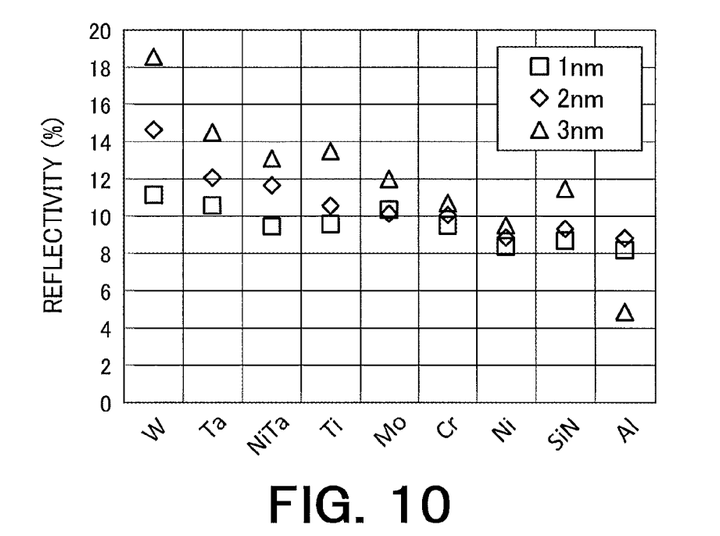
FIG. 10 is a view showing reflectivity when the thicknesses of several types of metal films are varied.
Figure 11:
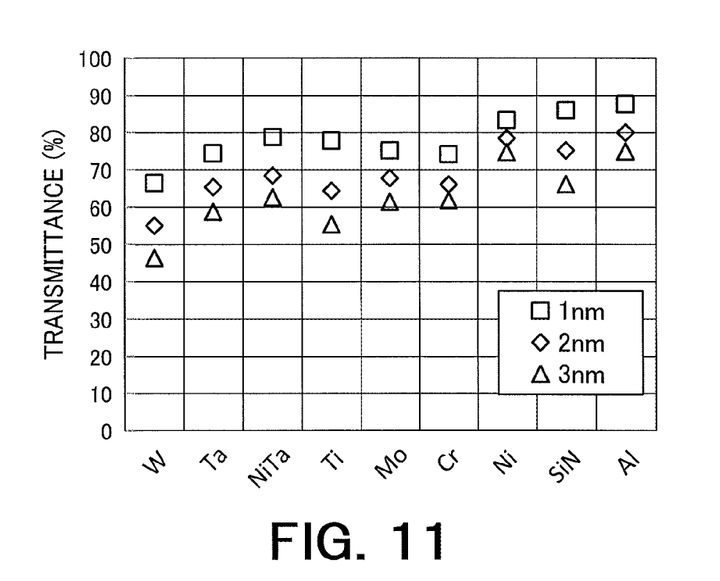
FIG. 11 is a view showing transmittance when the thicknesses of several types of metal films are varied.

It is desirable for the metal film to use a material with which the metal film can be formed having a several nm thin thickness. It is desirable for the metal film to use a material with which the metal film has a high reflectivity and a low transmittance even formed having a several nm thin thickness, in order to enhance interaction with a polarized component of inspection light. FIG. 10 shows reflectivity to 200 nm-light for metal materials of W, Ta, NiTa, Ti, Mo, Cr, Ni, SiN, and Al. FIG. 11 shows transmittance to the 200 nm-light for the same metal materials. It is found that reflectivity is high but transmittance is low for W, Ta, Ti, NiTa, and the like, at a several nm thickness. It is therefore desirable that W, Ta, Ti or NiTa is used for a reflection film in high accuracy inspection. An alloy of any of these metals and another metal may be used as the metal film. In other words, it is preferable that the metal film is made of a metal that contains at least one of elements of W, Ta, Ti, and Ni. Moreover, the metal film may be made of a metal that is at least one of W, Ta, Ti, and Ni, or an alloy of any one of these metals and another metal such as Cr, Mo, Al or Ag.

It is desirable that the metal film has a flat surface. A metal film with a large surface roughness is subjected to an increased line-pattern edge roughness which causes increase in noise of inspected images. For this reason, it is preferable that the metal film 103 has a small surface roughness, preferably, equal to or smaller than 3 nm so as not to increase the edge roughness of the concave-convex structure 102.

The metal film may be formed by a variety of film forming methods such as sputtering, vacuum deposition and CVD.

In the above description, although quartz is used for the template 100 to be inspected, Si, glass, etc. may be used.

As described above, the template defect inspection method of the first embodiment uses an inspection optical system having a polarization-rotation change amount provider that detects an amount of change in polarization rotation, from incident light, of a polarization component of linearly polarized light that is incident on a template from a light source via an optical system and is reflected by the template, and provides the amount of change in polarization rotation to an imaging device. By using the inspection optical system, linearly polarized light is incident on a template having a substrate that has a concave-convex structure formed thereon, and a metal film formed on the upper surface of and at least part of the side and bottom surfaces of the concave-convex structure. The amount of change in polarization rotation from incident light, of a polarization component of linearly polarized light incident on and then reflected by the template is detected and provided to the imaging device. It is preferable that the metal film has a thickness that is 5% to 20% of a half pitch hp of the line-and-space pattern of the concave-convex structure.

The template to be inspected may be a replica quartz template transferred from a master template. Although the replica template has an inverse structure of the master template, the metal film also gives an improved S/N ratio in principle, enabling accurate defect detection.

As described above, the first embodiment provides a template defect inspection method that can detect micro defects accurately.

Second Embodiment

A template defect inspection method according to a second embodiment will be explained. In the template defect inspection method according to the first embodiment, the template to be inspected has a concave-convex structure and a substrate each made of quartz, Si or glass. On the other hand, in the second embodiment, a template has a concave-convex structure made of a resin and a substrate made of quartz, Si, glass, etc. As for the inspection optical system, the one explained in the first embodiment, for example, the inspection optical system shown in FIG. 2A or FIG. 2B is used.

The template to be inspected by the template defect inspection method of the second embodiment has a resin-made concave-convex structure of a line-and-space pattern on a substrate, a metal film having a thickness that is about 5% to 20% of an hp, on the upper surface of the concave-convex structure, and a metal film having a thickness that is about 5% to 20% of a half pitch hp of the line-and-space pattern, on at least part of the side and bottom surfaces of the concave-convex structure.

In the second embodiment, like the first embodiment, it is preferable that the concave-convex structure has an hp smaller than a resolution limit that is determined by a wavelength of a light source of an inspection optical system and a numerical aperture of an objective lens of the inspection optical system.

In the second embodiment, like the first embodiment, it is preferable that the concave-convex structure has a height that is about ¼ of a wavelength of a light source. However, the height may be designed as required depending on the hp of the concave-convex structure.

In the second embodiment, like the first embodiment, the metal film preferably has a small surface roughness which is, more preferably, equal to or less than 3 nm, which preferably does not increase the edge roughness of the concave-convex structure.

In the second embodiment, it is preferable that the metal film has a strong interaction with incident light from a light source of an inspection optical system. Practically, it is preferable that the metal film is made of a metal such as W, Ta, Ti or Ni. Moreover, the metal film may be an alloy of W, Ta, Ti and Ni as main components, and another metal such as Cr, Mo, Al or Ag.

When a resin material is used for the concave-convex structure, like the second embodiment, the concave-convex structure can be formed by transfer from a master template 500 by nanoimprinting or the like. This replica template manufacturing method will be explained with reference to FIG. 12A to 12D.

Figure 12A:
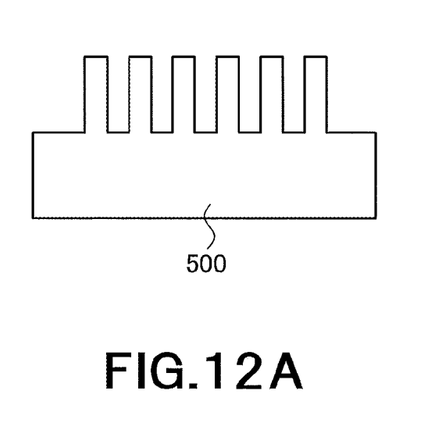
FIGS. 12A to 12D are sectional views showing a method of manufacturing a replica template.
Figure 12B:
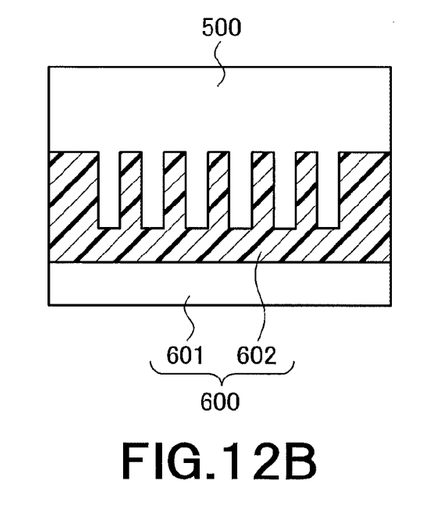
Figure 12C:
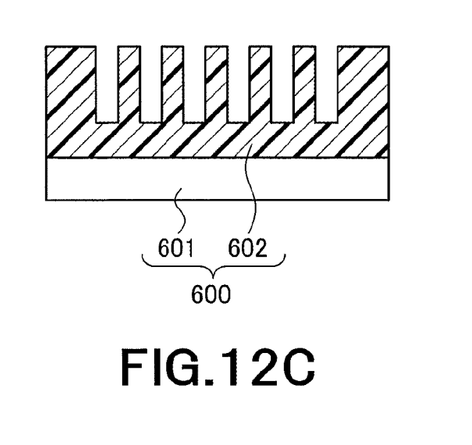
Figure 12D:
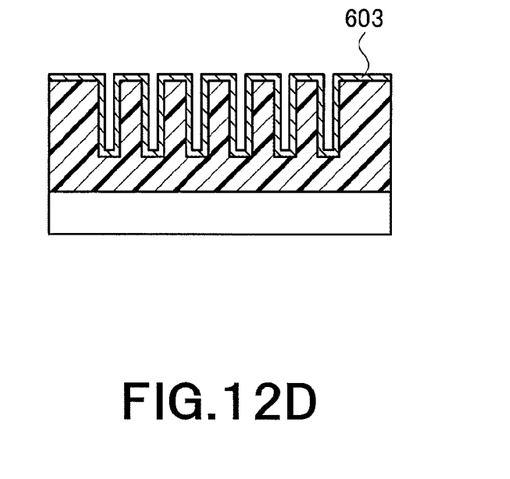

FIG. 12A shows a sectional view of the master template 500. As shown in FIG. 12B, a resin 602 is formed on a substrate 601. Thereafter, the master template 500 is pressed onto the resin 602, followed by hardening the resin 602 with ultraviolet rays, heat, etc. The master template 500 is then separated from the resin 602 to form a pattern-transferred replica template 600 (FIG. 12C). A metal film 603 is formed on the resin 602 of the replica template 600. Through the process, a replica template 600 having a metal film formed on a concave-convex structure is completed (FIG. 12D).

In the same manner as the first embodiment, replica templates each having a concave-convex structure with defects were formed and inspected for defects. As a result, every replica template showed an S/N ratio improved by about 1.4 times compared to a template having a concave-convex structure and a substrate, each made of quartz, with no metal film on the concave-convex structure, at a half pitch hp of the line-and-space pattern.

As described above, according to the second embodiment, accurate defect inspection is possible even by using a resin material for the concave-convex structure. Moreover, by using the replica template for inspection, the master template can be protected from contamination, degradation, etc.

As for the resin material, for example, a resist material and the like can be used. The resist material may be a silicon polymer, silsesquioxane, a cyclic olefin polymer, a norbornene resin that is a raw material of the cyclic olefin polymer, an oxazole resin, a block copolymer of amid acid and a silicon resin, etc. Like the first embodiment, quartz, Si, glass, etc. can be used as the substrate.

As described above, the second embodiment provides a template defect inspection method that can detect micro defects accurately.

Third Embodiment

A template defect inspection method according to a third embodiment is such that, in the template defect inspection method of the second embodiment, the template is a film substrate instead of a substrate of quartz, Si or glass. In detail, in the third embodiment, the template has a resin-made concave-convex structure and a film substrate. As for the inspection optical system, the one explained in the first embodiment, for example, the inspection optical system shown in FIG. 2A or FIG. 2B is used.

The template to be inspected by the template defect inspection method of the third embodiment has a resin-made concave-convex structure of a line-and-space pattern on a substrate, a metal film having a thickness that is about 5% to 20% of an hp, on the upper surface of the concave-convex structure, and a metal film having a thickness that is about 5% to 20% of a half pitch hp of the line-and-space pattern, on at least part of the side and bottom surfaces of the concave-convex structure.

In the third embodiment, like the second embodiment, it is preferable that the concave-convex structure has an hp smaller than a resolution limit that is determined by a wavelength of a light source of an inspection optical system and a numerical aperture of an objective lens of the inspection optical system.

In the third embodiment, like the second embodiment, it is preferable that the concave-convex structure has a height that is about ¼ of a wavelength of a light source. However, the height may be designed as required depending on the hp of the concave-convex structure.

In the third embodiment, like the second embodiment, the metal film preferably has a small surface roughness which is, more preferably, equal to or less than 3 nm, which preferably does not increase the edge roughness of the concave-convex structure.

Moreover, in the third embodiment, it is preferable that the metal film has a strong interaction with incident light from a light source of an inspection optical system. Practically, it is preferable that the metal film is made of a metal such as W, Ta, Ti or Ni. The metal film may be an alloy of W, Ta, Ti and Ni as main components, and another metal such as Cr, Mo, Al or Ag.

When a resin material is used for the concave-convex structure, like the third embodiment, the concave-convex structure is formed by transfer from the master template 500 by nanoimprinting or the like.

In the third embodiment, like the second embodiment, a replica template can be used as the template to be inspected, with a resin-made substrate.

As for the resin material, for example, a resist material and the like can be used. The resist material may be a silicon polymer, silsesquioxane, a cyclic olefin polymer, a norbornene resin that is a raw material of the cyclic olefin polymer, an oxazole resin, a block copolymer of amid acid and a silicon resin, etc.

As for the film substrate, polymethyl methacrylate, polyethylene, polypropylene, polyvinyl alcohol, polyethylene terephthalate, a fluorine-based resin, etc. can be used.

By using a resin-made film substrate, stretching in one- or two-dimension is possible to enlarge defects and inspect the enlarged defects, which enables detection of micro defects.

As described above, the third embodiment provides a template defect inspection method that can detect micro defects accurately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A template defect inspection method comprising:
emitting first light including a linearly polarized component to a template having a concave-convex structure in which a metal film is disposed on at least a part of the concave-convex structure to reflect second light including the linearly polarized component and a polarization-rotated component;
emitting the second light to a polarization beam splitter to output third light including the polarization-rotated component; and
detecting the third light including the polarization-rotated component.

2. The method of claim 1, wherein the concave-convex structure has a line-and-space pattern, and the metal film has a thickness that is 5% to 20% of a half pitch of the line-and-space pattern, on an upper surface of the concave-convex structure and on at least a part of side and bottom surfaces of the concave-convex structure.

3. The method of claim 1, wherein the metal film has a surface roughness equal to or less than 3 nm.

4. The method of claim 1, wherein the metal film includes at least one metal of W, Ta, Ti and Ni, or includes an alloy of the at least one metal.

5. The method of claim 1, wherein the concave-convex structure is disposed on a substrate, and the substrate and the concave-convex structure comprise either one of quartz, Si and glass.

6. The method of claim 1, wherein the concave-convex structure is disposed on a substrate, the substrate comprises either one of quartz, Si and glass, and the concave-convex structure comprises a resin.

7. The method of claim 1, wherein the concave-convex structure is disposed on a substrate, and the substrate and the concave-convex structure comprise a resin.

8. The method of claim 1, wherein the concave-convex structure is disposed on a substrate, the substrate comprises a resin, wherein the method comprises stretching the substrate to enlarge a defect.

9. The method of claim 1, wherein the first light is emitted by a light source, and the first light is focused to the template by an objective lens.

10. The method of claim 9, wherein the second light is emitted to the polarization beam splitter through a half wave plate and a Faraday rotator.

11. The method of claim 1, wherein the metal film is formed by a sputtering, a vacuum deposition or a chemical vapor deposition.

12. The method of claim 6, wherein the resin includes at least one of a silicon polymer, silsesquioxane, a cyclic olefin polymer, a norbornene resin that is a raw material of the cyclic olefin polymer, an oxazole resin, and a block copolymer of amid acid and a silicon resin.

13. The method of claim 7, wherein the resin includes at least one of a silicon polymer, silsesquioxane, a cyclic olefin polymer, a norbornene resin that is a raw material of the cyclic olefin polymer, an oxazole resin, and a block copolymer of amid acid and a silicon resin.

14. The method of claim 8, wherein the substrate includes at least one of polymethyl methacrylate, polyethylene, polypropylene, polyvinyl alcohol, polyethylene terephthalate, and a fluorine-based resin.

\* \* \* \* \*